(12) United States Patent
Kizer et al.

(10) Patent No.: US 8,231,586 B2
(45) Date of Patent: Jul. 31, 2012

(54) CEREBROSPINAL FLUID COLLECTION TUBES AND METHODS

(75) Inventors: Robert Kizer, Omaha, NE (US); Stephen M. Gross, Omaha, NE (US)

(73) Assignee: Creighton University, Omaha, NE (US)

( * ) Notice: Subject to any disclaimer, the term of this patent is extended or adjusted under 35 U.S.C. 154(b) by 205 days.

(21) Appl. No.: 12/310,949

(22) PCT Filed: Sep. 14, 2007

(86) PCT No.: PCT/US2007/019982
§ 371 (c)(1), (2), (4) Date: Mar. 13, 2009

(87) PCT Pub. No.: WO2008/033492
PCT Pub. Date: Mar. 20, 2008

(65) Prior Publication Data
US 2009/0204086 A1 Aug. 13, 2009

Related U.S. Application Data

(60) Provisional application No. 60/844,900, filed on Sep. 15, 2006.

(51) Int. Cl.
*A61M 5/32* (2006.01)
*A61B 5/00* (2006.01)
*B61D 81/00* (2006.01)
*A61D 5/00* (2006.01)

(52) U.S. Cl. ........ 604/263; 600/573; 600/576; 600/581; 604/264; 604/272

(58) Field of Classification Search .................. 600/573, 600/576, 581; 604/263, 264, 272
See application file for complete search history.

(56) References Cited

U.S. PATENT DOCUMENTS

| 1,518,531 | A | * | 12/1924 | Lung | 604/272 |
|---|---|---|---|---|---|
| 3,623,475 | A | * | 11/1971 | Sanz et al. | 600/575 |
| 3,712,302 | A | * | 1/1973 | Burke et al. | 604/110 |
| 4,024,857 | A | * | 5/1977 | Blecher et al. | 600/576 |
| 4,027,669 | A | * | 6/1977 | Johnston et al. | 604/110 |
| 4,266,544 | A | * | 5/1981 | Wardlaw | 604/110 |
| 4,529,096 | A | * | 7/1985 | Chartier et al. | 215/252 |
| 4,804,370 | A | * | 2/1989 | Haber et al. | 604/195 |

(Continued)

FOREIGN PATENT DOCUMENTS

GB   2 409 411 A   6/2005

(Continued)

OTHER PUBLICATIONS

Johnson, Kimberly S., M.D., Daniel J. Sexton, M.D., Cerebrospinal fluid: Physiology and utility of an examination in disease states, Sep. 2006.

*Primary Examiner* — Sean Dougherty
(74) *Attorney, Agent, or Firm* — Valauskas Corder LLC (57) ABSTRACT

A cerebrospinal fluid ("CSF") collection tube includes a bottom end portion and a tubular sidewall portion. The tubular sidewall portion has a first end and a second end, the first end being sealed to the bottom end portion and the second end defining an open end portion of the CSF collection tube. The CSF collection tube further includes a filament element that is attached to an interior surface of the tubular sidewall portion and projects through the open end portion of the CSF collection tube. The CSF collection tube may further include a removeable cap.

26 Claims, 5 Drawing Sheets

U.S. PATENT DOCUMENTS

| | | | |
|---|---|---|---|
| 4,808,381 A * | 2/1989 | McGregor et al. | 422/512 |
| 4,967,919 A * | 11/1990 | Earhart | 215/247 |
| 5,038,794 A * | 8/1991 | Van Valkenburg | 600/576 |
| 5,290,233 A * | 3/1994 | Campbell | 604/110 |
| 5,425,720 A * | 6/1995 | Rogalsky et al. | 604/198 |
| 5,885,255 A * | 3/1999 | Jaeger et al. | 604/192 |
| 5,891,093 A * | 4/1999 | Dysarz | 604/110 |
| 5,931,813 A * | 8/1999 | Liu | 604/110 |
| 6,102,894 A * | 8/2000 | Dysarz | 604/110 |
| 6,186,979 B1 * | 2/2001 | Dysarz | 604/110 |
| 6,235,003 B1 * | 5/2001 | Dysarz | 604/195 |
| 6,312,412 B1 * | 11/2001 | Saied et al. | 604/191 |
| 6,312,648 B1 * | 11/2001 | Lenardo et al. | 422/501 |
| 6,500,150 B1 * | 12/2002 | Gross et al. | 604/131 |
| 6,752,788 B2 * | 6/2004 | Tuen | 604/192 |
| 6,767,335 B1 * | 7/2004 | Helg | 604/110 |
| 6,843,782 B2 * | 1/2005 | Gross et al. | 604/141 |
| 6,846,293 B2 * | 1/2005 | Butler et al. | 600/573 |
| 7,393,345 B2 * | 7/2008 | Yang | 604/199 |
| 2002/0068882 A1 | 6/2002 | Butler et al. | |
| 2004/0253624 A1 | 12/2004 | Smith et al. | |
| 2006/0125142 A1 | 6/2006 | Kennedy et al. | |
| 2006/0135910 A1 * | 6/2006 | Luther et al. | 604/110 |
| 2007/0161852 A1 | 7/2007 | Raimondi | 600/104 |
| 2008/0015573 A1 * | 1/2008 | Rossi | 606/45 |
| 2009/0030343 A1 * | 1/2009 | Casarotto et al. | 600/576 |

FOREIGN PATENT DOCUMENTS

| | | |
|---|---|---|
| JP | 2003024436 A * | 1/2003 |
| WO | WO 9534335 A1 * | 12/1995 |
| WO | WO 9710016 A1 * | 3/1997 |

* cited by examiner

CEREBROSPINAL FLUID COLLECTION TUBES AND METHODS

This application claims priority from U.S. Provisional Patent Application No. 60/844,900 filed on Sep. 15, 2006.

FIELD OF THE INVENTION

The subject invention relates, generally, to medical devices and, more particularly, collection tubes for body fluids, such as cerebrospinal fluid.

BACKGROUND OF THE INVENTION

A spinal tap is a procedure which takes samples of a patient's cerebrospinal fluid ("CSF"). Spinal taps are performed when the physician suspects that the patient may have increased intracranial pressure (such as in pseudotumor cerebri) or an infection of the central nervous system (such as meningitis or encephalitis). These procedures are often performed in the emergency room but are also performed in a doctor's office or in a hospital setting.

Usually, before beginning a spinal tap procedure, the physician, or another medical professional arranges the contents of a spinal tap "kit" on a tray, positioned next to where the physician will be sitting to perform the procedure. The "kit" usually consists of four sterile tubes, a spinal needle (with a stylet inserted through the spinal needle), along with items for sterilizing the patient's skin, draping the patient, and measuring the intracranial pressure. Sometimes a test tube rack to hold the tubes is also built into the tray. Before the procedure, the physician or another medical professional removes all of these items from their sterile packaging, and arranges everything on the tray for easy access during the procedure.

Usually, the patient is asked to lie down on his or her side in a curled-up position, exposing the back. The physician then cleans and may numb the skin around the insertion point of the spinal needle. The physician then inserts a spinal needle, with a stylet inside the spinal needle, between the patient's vertebrae (usually in the L3-4 or L4-5 interspace) and advances the needle until the needle has reached the fluid-filled area surrounding the patient's spinal cord (commonly referred to as the dural space). The stylet is commonly used to prevent the tip of the spinal needle from becoming blocked by tissue as the needle is inserted through the patient's skin and other tissues, but some physicians prefer not to use the stylet. Once the needle is in place, the stylet is removed from the spinal needle. CSF flows through the needle and drips from the proximal end of the needle, which is known as the "hub" of the needle. The CSF is collected in the first test tube by holding it beneath the proximal end of the spinal needle. Once the desired amount of CSF (approximately 1 ml (or 1 cc) of CSF) is collected in the first test tube, the first test tube is set aside and a second test tube is held beneath the proximal end of the spinal needle to continue collection of the CSF as it drips from the proximal end of the spinal needle. The process is repeated until the desired amount of CSF is collected in the tubes.

Once collected; CSF is then sent to a laboratory to determine if the patient is suffering from viral (for example, Enteroviruses and Herpes viruses, as well as Arboviruses, Rabies or measles among other viral agents), bacterial (including *Haemophilus influenza, Streptococcus pneumoniae, Neisseria meningitidis*, and also *Listeria monocytogenes, Staphylococcus aureus, Mycobacterium tuberculosis, Escherichia coli* or other Gram negative enteric bacteria) or fungal (including *Cryptococcus neoformans, Coccidioides immiitis*, among other fungal agents) infection of the brain or supporting structures, among other possible diagnoses. The CSF is also examined for white and red blood counts and chemical components. The CSF can also be evaluated for the presence and amount of specific proteins, which may aid in the diagnosis of non-infectious nervous system ailments, such as Multiple Sclerosis.

The present procedure suffers from several drawbacks.

First, because of the difficulty in maintaining the collection tube under the proximal end of the spinal needle and the unpredictable nature of dripping fluids, CSF droplets are sometimes missed, or they run down the outside of the collection tube instead of into the collection tube.

Second, the proximal end of spinal needles typically includes a hub (e.g., a LUER-LOK™ hub). The CSF collects in the hub before forming droplets, and this mass of fluid in the spinal needle hub exacerbates the unpredictability of CSF drop formation and represents a volume of CSF that is not collected.

The procedure can be made more difficult if a patient is unable to remain calm or still, which is common when the patient is very young or very sick. In such cases the patient may need to be restrained, sedated, or both. Increasing the efficiency of CSF collection may reduce the duration of this procedure, which, in turn, may reduce the duration of time that the patient is restrained or given potentially dangerous sedative medications.

The CSF collection procedure also represents significant risk to the patient. Patients may develop severe side effects from the loss of too much CSF, including severe headaches. Increasing the efficiency of CSF collection may reduce the risks associated with excessive loss of CSF.

The risk of the patient moving and causing injury exists for the duration of the procedure. These risks include a risk of lacerating a spinal nerve, lacerating the meninges (causing permanent or persistent leaks of CSF) or bleeding, which complicates the Interpretation of laboratory results. These risks are increased in very young patients who are more likely to move during the procedure. Increasing the efficiency of CSF collection may reduce the duration of the procedure, which, in turn, would reduce these risks.

Failure to collect adequate amounts of CSF can result in a misdiagnosis or an absence of a definitive diagnosis. In the absence of a definitive diagnosis, the patient may not receive necessary treatment, may be subjected to inappropriate treatment, or may be treated in a manner which subjects the patient to a wide variety of medications to cover a broad range of potential ailments or infecting organisms. If mistreated, the patient's illness may worsen. Otherwise, the patient may be subjected to the potentially life threatening side effects of a broad range of treatments. Increasing the efficiency of CSF collection may aid in obtaining the correct diagnosis, which may reduce these risks.

For at least these reasons, there is a continuing need for methods and devices for collecting body fluids, in particular CSF, and the present invention satisfies this need.

SUMMARY OF THE INVENTION

The present invention relates to a CSF collection tube that includes a tubular sidewall portion with a bottom end portion and an open end portion. The CSF, collection tube further includes a filament element that projects through the open end portion of the CSF collection tube, and is attached to the tubular sidewall portion of the CSF collection tube by an attachment element.

It is contemplated the CSF collection tube may be any length, width and cross-sectional shape in order to collect adequate amounts of CSF. For example, the tubular sidewall portion may include any size and/or cross-sectional shape, such as circular cross-section, oval cross-section, polygonal cross-section, rectangular cross-section, square cross-section, or any other suitable cross-sectional shape. Additionally, the cross-sectional shape of the tubular sidewall portion may be uniform as well as non-uniform, such as tapered, varied or constricted to name a few. It is contemplated that the non-uniformity of the tubular sidewall portion may be positioned anywhere along the length of the CSF collection tube.

Likewise, the bottom end portion may be of any size and/or shape, for example, circular, oval, polygonal, planar, conical, hemispherical or square. The size and/or shape of the bottom end portion facilitates pipetting of the collected CSF or facilitates separation of solids by centrifugation. To facilitate standing the CSF collection tube in an upright position, in cases where the bottom end portion of the CSF collection tube is hemispherical or conical, the tubular sidewall portion can be extended downwardly past the region where the tubular sidewall portion is sealed to the bottom end portion so as to present a substantially planar bottom surface, or rim, that is substantially perpendicular to the tubular sidewall portion.

The bottom end portion of the CSF collection tube and the tubular sidewall portion of the CSF collection tube can be made of any suitable material or any combination of suitable materials. In one embodiment, the bottom end portion of the CSF collection tube and the tubular sidewall portion of the CSF collection tube are made of the same material. In another embodiment, the bottom end portion of the CSF collection tube and the tubular sidewall portion of the CSF collection tube are made of different materials. Examples of suitable materials include various kinds of polymers and copolymers (e.g., polystyrene), glass, ceramics, metals, and other materials that can be readily sterilized and/or that are inert to CSF (e.g., that substantially do not absorb or adsorb one or more CSF components, such as ions that substantially do not interact, such as binding, immunogenic responses, etc., with one or more CSF components).

Suitable overall dimensions of the CSF collection tubes described herein will be readily apparent to those skilled in the art, and they can be roughly the same as CSF collection tubes that are currently in use. For example, the CSF collection tube can have an outside diameter of from about 0.25 to about 1.25 inches, e.g., from about 0.375 to about 1 inch, from about 0.5 to about 0.75 inch, of about 0.625 inch, from 0.25 to 1.25 inches, from 0.375 to 1 inch, and/or from 0.5 to 0.75 inch and a length of from about 2 inches to about 6 inches, e.g., from about 2.5 inches to about 5.5 inches, from about 3 inches to about 5 inches, from about 3.5 inches to about 4.5 inches, of about 4 inches, from 2 inches to 6 inches, from 2.5 inches to 5.5 inches, from 3 inches to 5 inches, and/or from 3.5 inches to 4.5 inches.

Optionally, the tubular sidewall portion of the CSF collection tube can also be marked with one or more volume graduations, for example, from 0.5 to 4 ml in 0.1, 0.2, or 0.5 ml increments. The volume graduations can be marked, for example, by etching the surface of the tubular sidewall portion, with raised markings, and/or with paint or other such surface-applied marking.

The CSF collection tubes of the present invention can be sterilized or not sterilized. Where sterilized, the CSF collection tubes of the present invention can be provided in sealed packaging designed to maintain sterility.

The CSF collection tube according to the present invention can be provided as part of a kit, to which the present invention also relates. Such a kit includes one or more CSF collection tubes in accordance with the present invention and one or more of the following: a spinal needle (with or without a stylet inserted through the spinal needle), one or more items for sterilizing a patient's skin, one or more items for draping the patient, a tray, and a rack for holding the CSF collection tube or tubes in an upright position.

The filament element is attached to the CSF collection tube by an attachment element such that it projects through, or outside, the CSF collection tube. The attachment element can directly or indirectly attach the filament element to the collection tube. A direct attachment element includes, for example, integral attachment, adhesive, solvent welding, or heat welding. Integral attachment includes forming the filament element and the tubular sidewall portion and optionally the bottom end portion in a single step, for example, by injection molding or spin casting. An indirect attachment includes, for example, a structure component such as a bridge component or platform component that attaches to the CSF collection tube and to the filament element. Structure components can be attached to the CSF collection tube, and further the filament element attached to the structure component by any of the methods described herein, such as integral attachment, adhesive, solvent welding, heat welding, injection molded or spin casting.

The filament element may be directly attached to the tubular sidewall portion at any convenient location. In embodiments where the filament element is indirectly attached to the tubular sidewall portion via a structure component, the structure component can be attached to the tubular sidewall portion at any convenient location. For example, the filament element, and optionally a structure component, can be attached to the tubular sidewall portion at a position "X", where "X" is the distance from the open end portion of the CSF collection tube. "X" can be, for example, between about 0.001 L and about 0.5 L, such as between about 0.02 L and about 0.4 L, between about 0.03 L and about 0.25 L, between about 0.04 L and about 0.1 L, between about 0.05 L and about 0.08 L, between 0.0.01 L and 0.5 L, between 0.02 L and 0.4 L, between 0.03 L and 0.25 L, between 0.04 L and 0.1 L, and/or between 0.05 L and 0.08 L. "X" can also be, for example, from about 2 mm to about 50 mm, such as from about 3 mm to about 40 mm, from about 4 mm to about 35 mm, from about 5 mm to about 30 mm, from about 6 mm to about 25 mm, from about 7 mm to about 20 mm, from about 8 mm to about 15 mm, about 8 mm, about 9 mm, about 10 mm, about 11 mm, about 12 mm, about 13 mm, about 14 mm, about 15 mm, from 2 mm to 50 mm, from 3 mm to 40 mm, from 4 mm to 35 mm, from 5 mm to 30 mm, from 6 mm to 25 mm, from 7 mm to 20 mm, from 8 mm to 15 mm, from 9 mm to 14 mm, from 10 mm to 14 mm, from 10 mm to 13 mm, and/or from 11 mm to 13 mm.

Once attached, the filament element may achieve an extended position, or project through the open end portion of the CSF collection tube. The filament element may project at any angle relative to a cross-sectional plane of the CSF collection tube. This angle can range from about 1° to 90° (perpendicular), such as from about 20° to about 80°, from about 30° to about 70°, from about 40° to about 60°, about 35°, about 40°, about 45°, about 50°, about 55°, about 60°, about 65°, from 10° to 90° (perpendicular), from 20° to 80°, from 30° to 70°, from 35° to 65°, from 40° to 60°, and/or from 45° to 55°.

The filament element is flexible and can flex (or otherwise move) between an extended position, in which the filament element projects through the open end portion of the CSF collection tube, and a retracted position, in which the filament element does not project through the open end portion of CSF collection tube.

A flexible filament that projects through the open end portion of the CSF collection tube allows the filament to contact the spinal needle hub such that all necessary fluid is collected, minimizing waste. Also, a flexible filament permits an angle at which to hold the CSF collection tube that is comfortable or ideal for the person performing the procedure, for example, the CSF collection tube may be held in the vertical position, in the near horizontal position or anywhere in between. In embodiments where the CSF collection tube includes a removable cap, the flexible filament retracts into the CSF collection tube upon sealing the open end portion. When the CSF is analyzed in a laboratory, the CSF can be removed, transferred or measured from the CSF collection tube, for example by inserting a pipette or other device into the CSF collection tube. The flexible filament reduces interference with the device, or pipette, to be inserted into the CSF collection tube for removal, transfer or measurement of the CSF The filament element can be made of any suitable material or any combination of suitable materials. The filament element can be made of the same material as the tubular sidewall portion of the CSF collection tube and/or of the same material as the bottom end portion of the CSF collection tube, or the filament element can be made of a different material. Examples of the materials from which the filament element can be made, include polymers, copolymers, glass, ceramics, metals, and other materials that can be readily sterilized. For example, in one embodiment, the filament element can be made of polystyrene. In another embodiment, the filament element includes a polymer or a copolymer that is coated with a coating, for example, a coating that increases the filament element's wetability. "Wetability", as used herein, is meant to refer to the ability of CSF to flow along the filament element and can be determined, for example, by measuring the CSF contact angle in the presence and absence of coating. In still other embodiments, the filament element can include a polymer or a copolymer that is coated with a coating that improves the lubricity of the filament element to CSF. In yet another embodiment, the filament element can include a polymer or a copolymer that is coated with a coating that imparts an inertness toward CSF, for example, to reduce or prevent absorption or adsorption of one or more CSF components, such as ions, to reduce or prevent other undesirable interactions, such as binding, immunogenic responses, etc., between the coating and one or more CSF components. It will be appreciated that the coating can be selected to impart combinations of these or other properties (such as increased wetability, improved lubricity, and inertness) to the filament element. Other considerations in selecting a material (or combination of materials) from which the filament element may be made include the flexibility, stiffness, strength, and other mechanical properties of the material, as well as the inertness of the material to CSF. It may be desirable to use a coated filament element in which the material for the filament element is selected based on the desired flexibility, stiffness, strength, and other mechanical properties of the material and in which the material for the coating is selected based oh the desired surface and chemical properties of the material.

For example, in one embodiment, the bottom end portion, the tubular sidewall portion, and the filament element include the same polymer or copolymer and the filament element further includes a coating which increases the filament element's wetability. In another embodiment, the bottom end portion, the tubular sidewall portion, and the filament element include the same polymer or copolymer and are integrally formed, for example, by injection molding and in yet another embodiment, the filament element further includes a coating which increases the filament element's wetability.

The filament element can have any contemplated surface structure and be solid or hollow, and it can be of any convenient diameter and/or cross-sectional shape. For example, the filament element can have an outer diameter of from about 0.05 mm to about 2 mm, such as from about 0.1 mm to about 1.5 mm, from about 0.2 mm to about 1.2 mm, from about 0.3 mm to about 1 mm, from about 0.5 mm to about 1 mm, about 0.2 mm, about 0.3 mm, about 0.4 mm, about 0.5 mm, about 0.6 mm, about 0.7 mm, about 0.8 mm, about 0.9 mm, about 1 mm, etc. In the case of hollow filament elements, the properties of the filament element are such that CSF is not drawn into the hollow of the filament element. For example, the inner diameter of a hollow filament element can be selected so as to be sufficiently small such that CSF is not drawn into the hollow of the filament element. As mentioned above, the filament element can be of any convenient cross-sectional shape. For example, circular, oval, triangular, square, hexagonal, rectangular, crescent and elliptical cross-sectional shapes are suitable, as are other cross-sectional shapes such as those having large aspect ratios such as one dimension being 2 or more times, such as 3 or more times, 4 or more times, 5 or more times, 8 or more times, 10 or more times, 20 or more times, 50 or more times, the other dimension. The filament element's cross-sectional shape and/or the surface structure can be selected so as to increase the filament element's wetability, and/or lubricity towards CSF.

In other embodiments of the present invention, the CSF collection tube includes a removeable cap, for example a snap-on cap or screw-on cap, although other types of removable caps may also be employed. The cap is sized and configured so as to seal the open end portion of the CSF collection tube. Additionally, a connecting element connects the cap to the CSF collection tube, for example, by a flexible tab, which in turn, can be attached to the CSF collection tube by a ring positioned around the CSF collection tube.

In certain embodiments of the present invention with a removeable cap, the flexible filament element moves between an extended position and a retracted position. When positioned to seal the open end portion of the CSF collection tube, the cap causes the filament element to assume a retracted position. Once the cap is removed, the filament element assumes an extended position in which the filament element projects through the open end portion of the CSF collection tube.

The present invention relates also to a method for collecting CSF from a patient. The method includes providing a spinal needle having distal end and a proximal end, the distal end having a tip and the proximal end having a hub. The method further includes supplying a CSF collection tube having a filament element. The spinal needle is inserted between a patients vertebrae until the tip of the spinal needle reaches a dural space. The CSF collection tube's filament element is placed into the spinal needle's hub, and CSF is permitted to flow along the filament element from the spinal needle's hub and into the CSF collection tube until the CSF collection tube contains a sufficient amount of CSF. The method further includes removing the spinal needle from the patient.

An object of the present invention is to provide a more efficient procedure of CSF collection, and possibly reduce the risks associated with spinal tap procedures.

Another object of the present invention is to increase predictability of CSF collection.

Another object of the present invention is to decrease the duration of time for a spinal tap procedure.

Yet another object of the present invention is to reduce the amount of CSF lost or wasted during a spinal tap procedure.

The present invention and its attributes and advantages will be further understood and appreciated with reference to the detailed description below of presently contemplated embodiments, taken in conjunction with the accompanying drawings.

DETAILED DESCRIPTION OF EMBODIMENTS OF THE INVENTION

The present invention relates to a CSF collection tube. As shown generally in FIG. 1, the CSF collection tube 100 includes a bottom end portion 200 integrally connected to a tubular sidewall portion 300. The CSF collection tube 100 further includes a filament element 400 that projects through an open end portion 500 of the CSF collection tube 100, and is attached to the CSF collection tube by an attachment element 600.

Figure 1:
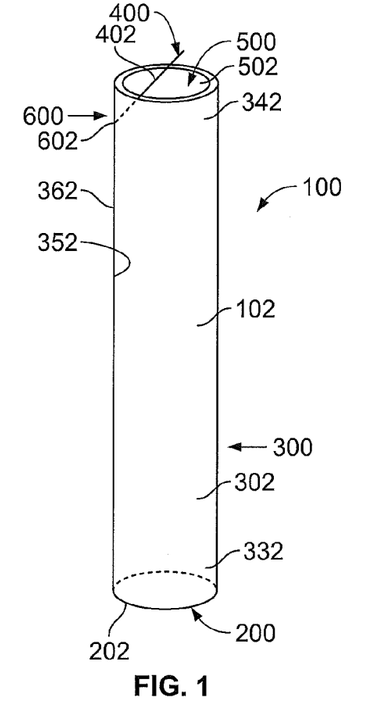
FIG. 1 is illustrates one embodiment of a cerebrospinal fluid ("CSF") collection tube according to the present invention.

As shown more specifically in FIG. 1, one embodiment of a CSF collection tube 102 includes a circular bottom end portion 202 and a circular cross-sectional tubular sidewall portion 302. Tubular sidewall portion 302 has first end 332 and second end 342 as well as an interior surface 352 and an exterior surface 362. The first end 332 of the tubular sidewall portion 302 is sealed to bottom end portion 202 of CSF collection tube 102. The second end 342 of the tubular sidewall portion 302 defines a circular open end portion 502.

In the embodiment illustrated of FIG. 1, CSF collection tube 102 includes filament element 402 that is integrally attached 602 to interior surface 352 of tubular sidewall portion 302. Filament element 402 projects through open end portion 502 of CSF collection tube 102. Filament element 402 is shown as projecting through open end portion 502 of CSF collection tube 102 at an angle (relative to a cross-sectional plane of the CSF collection tube 102, such as open end portion 502). As shown in FIG. 1, filament element 402 is angled at approximately 45°, although any angle is contemplated such as including and between the range from 10° to 90°.

Although tubular sidewall portion 102 is illustrated as having a substantially uniform circular cross-sectional shape, non-uniform cross-sections as well as other cross-sectional shapes are contemplated, such as circular, oval, polygonal, rectangular and square to name a few.

Figure 2:
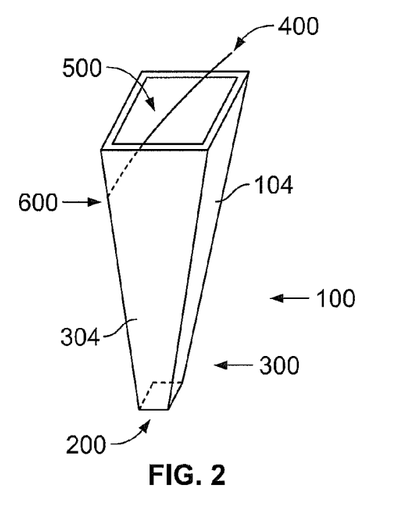
FIG. 2 is an alternate embodiment of a CSF collection tube according to the present invention.
Figure 3:
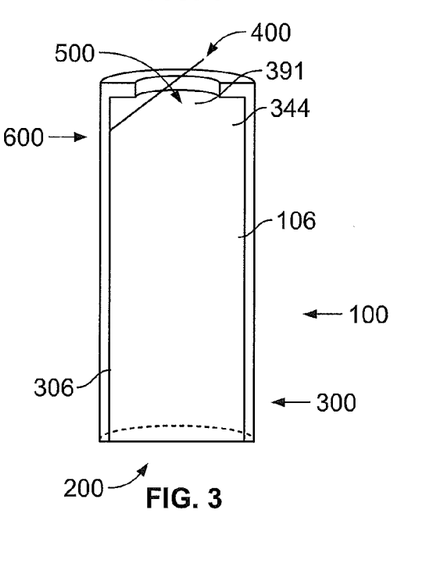
FIG. 3 is an alternate embodiment of a CSF collection tube according to the present invention.
Figure 4:
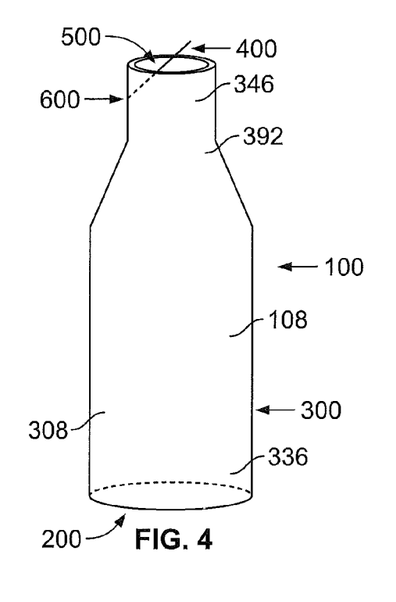
FIG. 4 is an alternate embodiment of a CSF collection tube according to the present invention.

FIGS. 2-4 illustrate alternate embodiments of the CSF collection tube 100 including various cross-sectional configurations. FIG. 2 illustrates CSF collection tube 104 with a tubular sidewall portion 304 having a non-uniform tapered square cross-sectional shape. FIG. 3 illustrates CSF collection tube 106 with a tubular sidewall portion 306 having a non-uniform constricted circular cross-sectional shape. As shown in FIG. 3, constriction 391 is shown at the second end 344 of the tubular sidewall portion 306 of CSF collection tube 106. As shown in FIG. 4, constriction 392 is shown substantially between the second end 346 and the first end 336 of tubular sidewall portion 308 of CSF collection tube 108.

Figures 5, 6, 7:
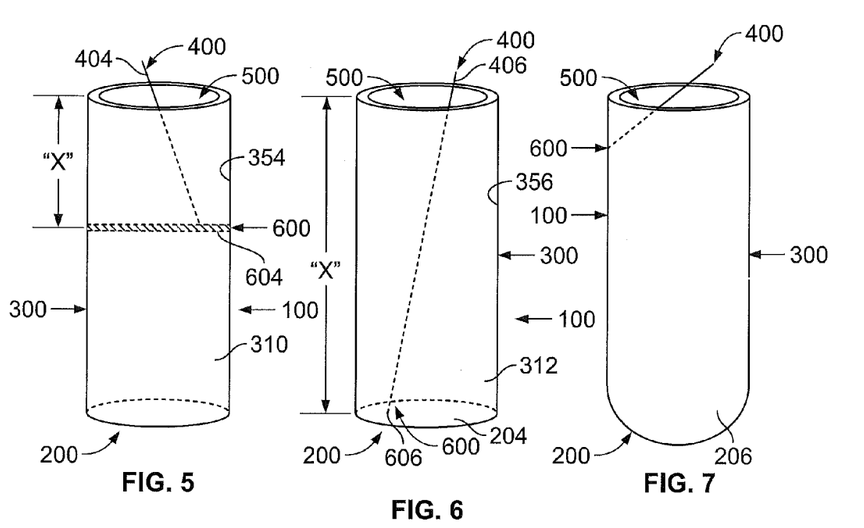
FIG. 5 is an alternate embodiment of a CSF collection tube according to the present invention.
FIG. 6 is an alternate embodiment of a CSF collection tube according to the present invention.
FIG. 7 is an alternate embodiment of a CSF collection tube according to the present invention.

FIGS. 5 and 6 illustrate alternate embodiments of the attachment element 600 that attaches the filament element 400 to the tubular sidewall portion 300 of the CSF collection tube 100. As shown in FIG. 5, the filament element 404 is attached indirectly to the interior surface 354 of the tubular sidewall portion 310 by an attachment element 600, here a bridge component 604. The filament element 404 is attached to bridge component 604 that is, in turn, attached to interior surface 354 of tubular sidewall portion 310. As further illustrated in FIG. 6, the attachment element 600 is an integral attachment 606 of the filament element 406 to the interior surface 356 of tubular sidewall portion 312 by attaching filament element 406 to the bottom end portion 204. The integral attachment 606 forms the filament element 406 and the bottom end portion 204 of the tubular sidewall portion 312 by injection molding, or spin casting.

Also illustrated in FIGS. 5 and 6, the filament element 400 is attached to the tubular sidewall portion 300 at a position "X", where "X" is the distance from open end portion of CSF collection tube 100 to the filament element 400 attachment point. As shown in FIG. 5, filament element 404 is positioned at approximately 0.15 L, although any position is contemplated such as including and between the range from 0.01 L and 0.5 L As shown in FIG. 6, filament element 406 is positioned at approximately 49 mm, although any position is contemplated such as including and between the range from 2 mm to 50 mm.

Figures 8, 9A, 9B:
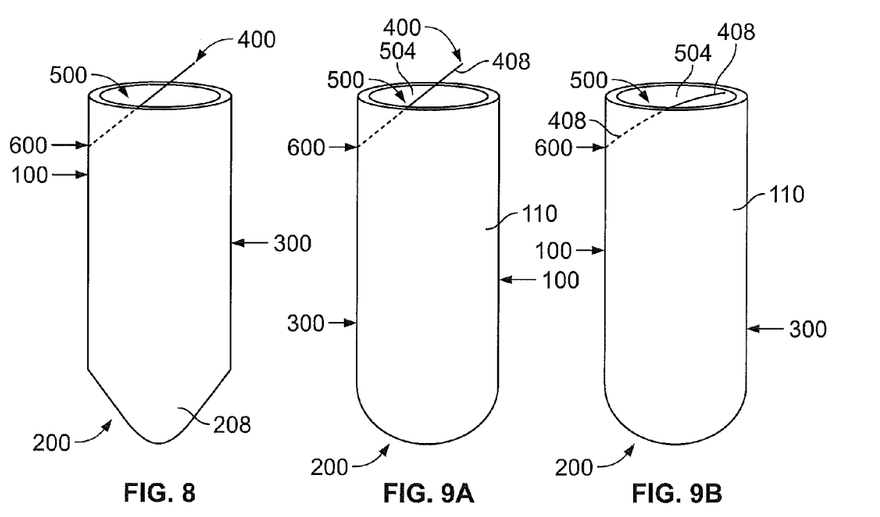
FIG. 8 is an alternate embodiment of a CSF collection tube according to the present invention.
FIG. 9A illustrates an embodiment of a CSF collection tube including a filament element in an extended position according to the present invention.
FIG. 9B illustrates an embodiment of a CSF collection tube including a filament element in a retracted position according to the present invention.
Figure 10A:
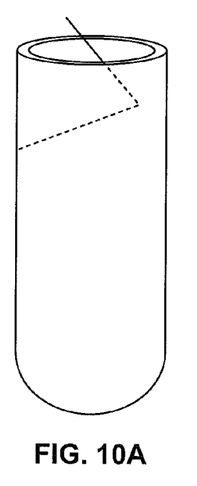
FIGS. 10A-10F illustrate various embodiments of the filament element of a CSF collection tube according to the present invention.
Figure 10B:
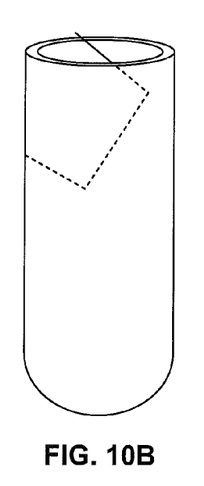
Figure 10C:
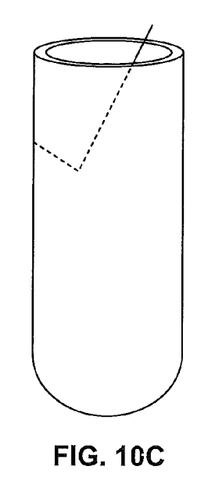
Figure 10D:
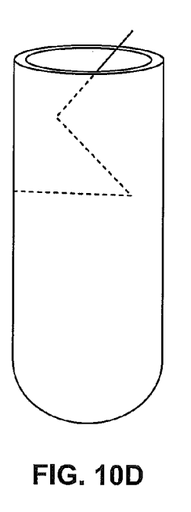
Figure 10E:
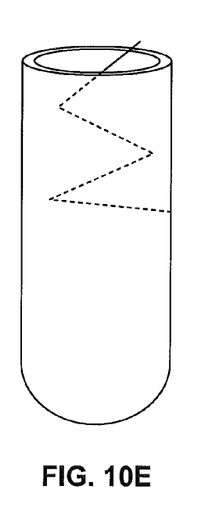
Figure 10F:
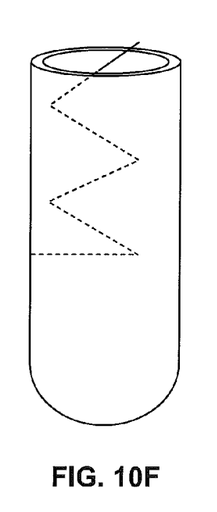

In FIGS. 1-6, the bottom end portion 200 of the CSF collection tube 100 has been illustrated as being substantially flat, or planar. However, additional embodiments of the bottom end portion 200 of the CSF collection tube 100 are contemplated, such as a hemispherical bottom portion 206 as shown in FIG. 7 or conical bottom portion 208 as illustrated in FIG. 8. The size and/or shape of the bottom end portion facilitates pipetting of the collected CSF or facilitates separation of solids by centrifugation.

In certain embodiments of the present invention, the filament element 400 is flexible and can flex (or otherwise move) between an extended position and a retracted position. As illustrated in FIG. 9A, the filament element 408 is in an extended position and projects through the open end portion 504' of the CSF collection tube 110. As illustrated in FIG. 9B, the filament element 408 is in a retracted position and does not project through the open end portion 504 of the CSF collection tube 110. A number of filament element configurations can be used to achieve this result, and some of these are illustrated in FIGS. 10A-10F (in the extended position).

Figure 11:
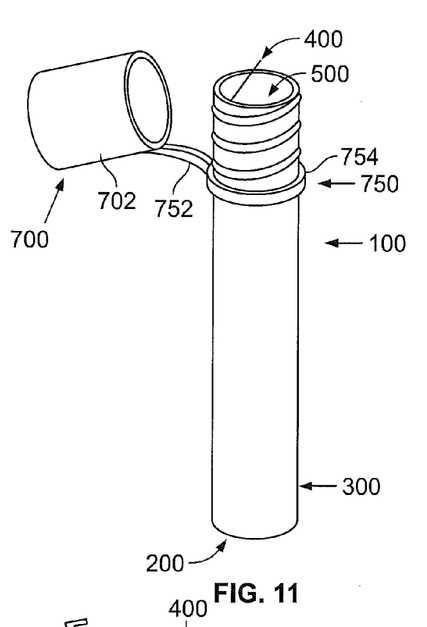
FIG. 11 illustrates an embodiment of a CSF collection tube including a removable cap according to the present invention.
Figure 12:
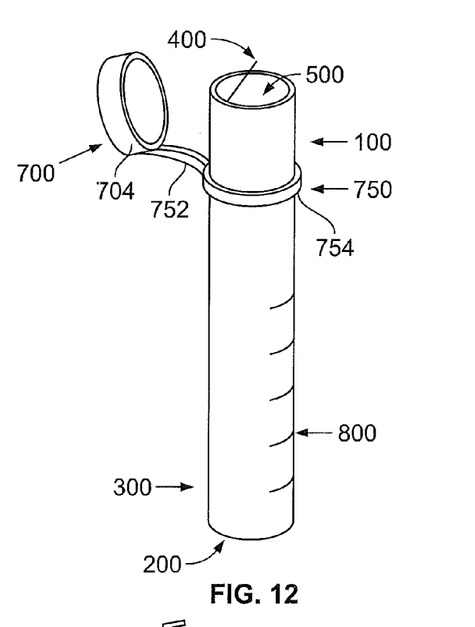
FIG. 12 illustrates an alternate embodiment of a CSF collection tube including a removable cap according to the present invention.

In other embodiments of the present invention, the CSF collection tube 100 includes a removable cap 700, for example a snap-on cap or screw-on cap. As illustrated in FIGS. 11 and 12, CSF collection tube 100 can further include removable cap 700 that is sized and configured so as to seal the CSF collection tube 100.

FIG. 11 shows a screw-on cap 702, while FIG. 12 shows a snap-on cap 704. As shown, the cap 700 can be connected to CSF collection tube 100 by a connecting element 750, for example, by flexible tab 752, which, in turn, can be attached to CSF collection tube 100 by ring 754 positioned around the tubular sidewall portion 300 of the CSF collection tube 100.

Optionally, the tubular sidewall portion of the CSF collection tubes of the present invention can also be marked with one or more volume graduations (e.g., from 0.5 to 4 ml in 0.1, 0.2, or 0.5 ml increments). The volume graduations can be marked, for example, by etching the surface of the tubular sidewall portion, with raised markings, and/or with paint or other such surface-applied marking. Such optional markings are illustrated in FIG. 12 as volume graduation markings 800.

Figure 13A:
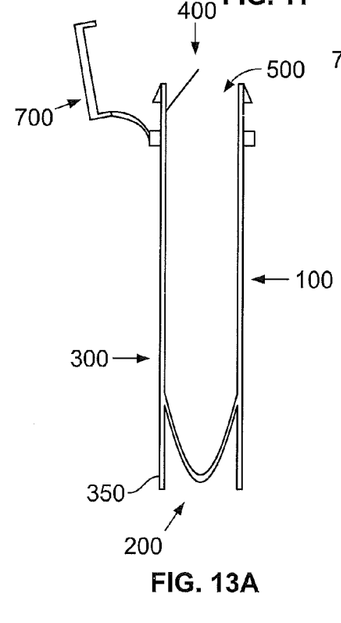
FIG. 13A-C illustrates an alternate embodiment of a CSF collection tube including a removable cap to permit the filament element to flex between an extended position and a retracted position according to the present invention.
Figures 13B, 13C:
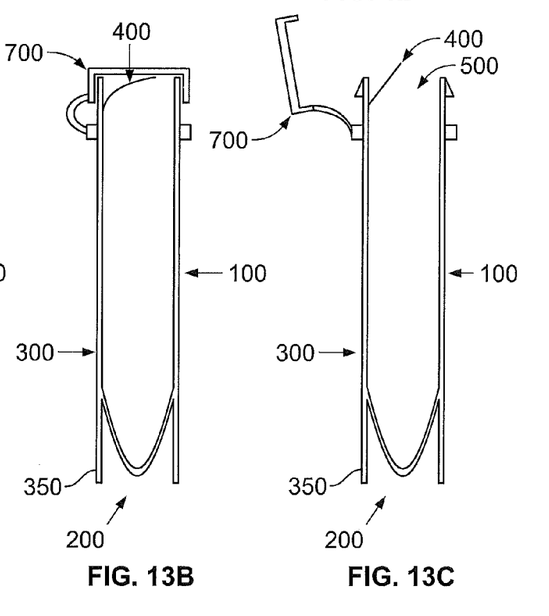

As shown in FIGS. 13A-C, certain embodiments of the present invention with a removeable cap permit the filament element to flex between an extended position and a retracted position. In FIG. 13A, the cap 700 is removed, and filament element 400 is in an extended position in which filament element 400 projects through open end portion 500 of CSF collection tube 100. Turning now to FIG. 13B, upon positioning cap 700 to seal the open end portion 500 of the CSF collection tube 100, cap 700 engages filament element 400 and causes filament element 400 to assume a retracted position in which filament element 400 does not project through the open end portion 500 of CSF collection tube 100. Referring now to FIG. 13C, upon removing the cap 700 from CSF collection tube 100, cap 700 disengages from filament element 400 and permits filament element 400 to again assume an extended position in which filament element 400 projects through the open end portion 500 of the CSF collection tube 100.

As mentioned above, and also illustrated in FIGS. 13A-C to facilitate standing the CSF collection tube 100 in an upright position, in cases where the bottom end portion 200 of the CSF collection tube is hemispherical or conical, the tubular sidewall portion 300 can be extended downwardly past the region where the tubular sidewall portion 300 is sealed to the bottom end portion 200 so as to present a substantially planar bottom surface or rim 350 that is substantially perpendicular to the tubular sidewall portion 300.

The CSF collection tubes of the present invention can be used to collect CSF from a patient, for example, using the method described below, to which method the present invention also relates.

The present invention relates also to a method for collecting CSF from a patient. The method includes providing a spinal needle having distal end and a proximal end, the distal end having a tip and the proximal end having a hub. The method further includes supplying a CSF collection tube having a filament element projecting, from the CSF collection tube's interior. The spinal needle is inserted between a patients vertebrae until the tip of the spinal needle reaches a dural space. The CSF collection tube's filament element is placed into the spinal needle's hub, and CSF is permitted to flow along the filament element from the spinal needle's hub and into the CSF collection tube until the CSF collection tube contains a sufficient amount of CSF. The method further includes removing the spinal needle from the patient.

Figure 14:
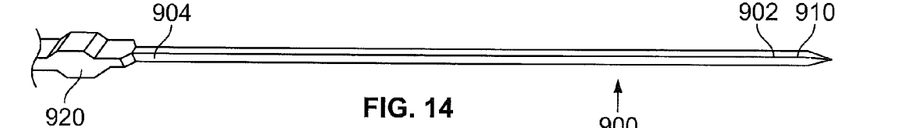
FIG. 14 illustrates a spinal needle according to the present invention.

FIG. 14 illustrates a spinal needle 900 suitable for use in the method according to the present invention. Referring to FIG. 14, there is shown spinal needle 900 having distal end 902 and a proximal end 904. Distal end 902 has tip 910, and proximal end 904 has hub 920. One spinal needle suitable for use in the method of the present invention is an 22 G, 3½ inch (1.27 mm×8.89 cm), LUER-LOK™ hub spinal needle with a Quincke-type point, available through Becton-Dickinson, Franklin Lakes N.J. (reorder No. 405181). The spinal needle can be used with or without a stylet (not illustrated).

Figure 15:
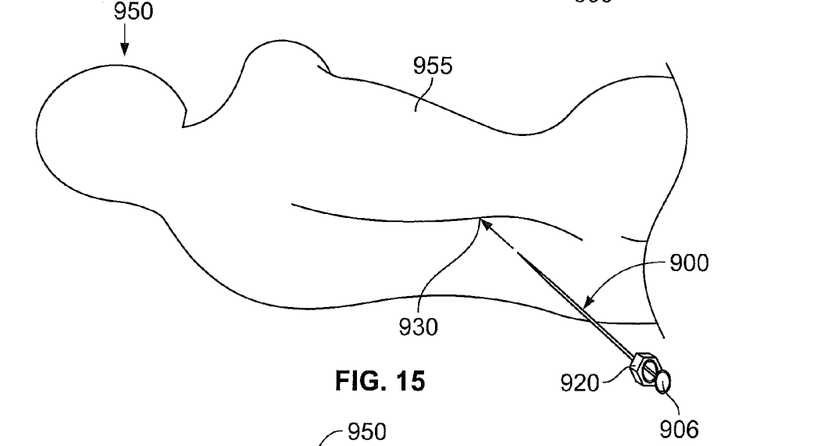
FIG. 15 illustrates a patient prepared for a spinal tap procedure according to the present invention.

Referring to FIG. 15, the patient 950 is typically prepared for the needle insertion by placing the patient 950 on his or her side, exposing back 955. The skin of the patient's back 955 around insertion site 930 is sterilized, and, optionally, the skin around insertion site 930 can be numbed. Spinal needle 900 (optionally with stylet 906 inserted through spinal needle 900) is inserted at insertion site 930 between the patient's vertebrae (e.g., in the patient's L3-4 or L4-5 interspace), and needle 900 is advanced until it reaches a dural space. If stylet 906 is employed, it is withdrawn from spinal needle 900.

Figure 16:
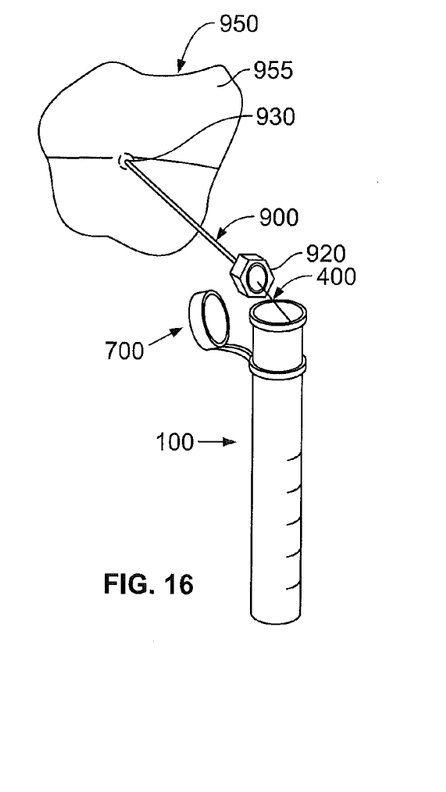
FIG. 16 illustrates a spinal tap procedure according to the present Invention.

A CSF collection tube 100 according the embodiments described herein is used by placing the filament element 400 into the hub 920 of the spinal needle 900, as shown in FIG. 16. CSF is permitted to flow along filament element 400 from the hub 920 of the spinal needle 900 and into the CSF collection tube 100. CSF collection is continued in this manner until CSF collection tube 100 contains a sufficient amount of CSF, for example, as indicated by the volume graduations markings 800 on CSF collection tube 100.

Typically, 1-5 ml of CSF is collected, depending, for example, on the age of the patient, the condition of the patient, and the tests to be performed on the CSF. Frequently, it is desirable to collect this volume in multiple CSF collection tubes. This can be readily achieved using the method of the present invention by removing the filament element 400 from the hub 920 of the spinal needle 900, setting the CSF collection tube 100 aside, providing a second (or third or fourth) CSF collection tube 100, placing the second (or third or fourth) filament element 400 of the CSF collection tube 100 into hub 920 of spinal needle 900, and permitting CSF to flow along the second (or third or fourth) filament element from the hub 920 and into the second (or third or fourth) CSF collection tube 100. While one CSF collection tube is being replaced with the next CSF collection tube, any CSF which enters the hub is retained in the hub until a sufficient amount collects in the hub to form a drop. This delay in drop formation reduces the likelihood of CSF loss during the time it takes to swap CSF collection tubes.

Once the desired amount of CSF is collected in the CSF collection tube (or in two, three, four, five, or more collection tubes), spinal needle 900 is removed from the patient 950. Where employed, stylet 906 can be re-inserted through spinal needle 900 prior to removing the needle 900 from the patient 950. With embodiments where collection tube 100 includes a removable cap 700, removable cap 700 can be positioned to seal the open end portion of the CSF collection tube.

It will be appreciated that the above collection tubes have been described and detailed with respect to the collection of CSF. However, as one skilled in the art will appreciate, these tubes can be used for the collection of other fluids, especially in the context of medical procedures. Accordingly, the present invention is also directed to fluid collection tubes generally, which fluid collection tubes can be used for collecting CSF (as described above) as well as for collecting other body fluids, such as tears, sinus fluids, ear fluids, puss or other fluids from blisters, wounds, lesions, or other skin defects when the collection is carried out via a needle (e.g., a needle with a hub) without aspiration. The collection tubes to be used for collection fluids other than CSF can be the same as the ones used for CSF, or they can be particularly adapted for the collection of the other fluids (e.g., by optimizing tube size, filament element coating, etc. for the particular fluid or fluids to be collected).

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A cerebrospinal fluid ("CSF") collection tube comprising:
    a bottom end portion;
    a tubular sidewall portion with a first end and a second end having an interior surface and an exterior surface, wherein said first end is sealed to said bottom end portion and wherein said second end defines an open end portion;
    a filament element configured to collect fluid, wherein said filament element includes a first end and a second end; and
    an attachment element, wherein said attachment element directly attaches said first end of said filament element to said interior surface of said tubular sidewall portion;
    wherein said filament element is flexible and can move between an extended position in which said filament element projects through said open end portion and a retracted position in which said filament element does not project through said open end portion; and
    a removable cap sized and configured so as to seal said open end portion wherein said cap causes said filament element to assume a retracted position when said cap is positioned to seal said open end portion..

2. The cerebrospinal fluid ("CSF") collection tube according to claim 1, wherein said second end of said filament element projects through said open end portion.

3. The cerebrospinal fluid ("CSF") collection tube according to claim 1:
    a connecting element, wherein said connecting element connects said cap to said tubular sidewall portion.

4. The cerebrospinal fluid ("CSF") collection tube according to claim 1, wherein said cap is a snap-on cap.

5. The cerebrospinal fluid ("CSF") collection tube according to claim 1, wherein said cap is a screw-on cap.

6. The cerebrospinal fluid ("CSF") collection tube according to claim 1, wherein said cap is a snap-on cap.

7. The cerebrospinal fluid ("CSF") collection tube according to claim 1, wherein said cap is a screw-on cap.

8. The cerebrospinal fluid ("CSF") collection tube according to claim 1, wherein said attachment element is a structure component.

9. The cerebrospinal fluid ("CSF") collection tube according to claim 1, wherein said attachment element an integral attachment.

10. The cerebrospinal fluid ("CSF") collection tube according to claim 1, wherein said attachment element is an adhesive.

11. The cerebrospinal fluid ("CSF") collection tube according to claim 1, wherein said attachment element is a weld.

12. The cerebrospinal fluid ("CSF") collection tube according to claim 1, wherein said filament element comprises a material selected from the group consisting of polymer, copolymer, ceramic, metal, glass, and combinations of polymer, copolymer, ceramic, metal, and glass.

13. The cerebrospinal fluid ("CSF") collection tube according to claim 1, wherein said filament element comprises a polymer.

14. The cerebrospinal fluid ("CSF") collection tube according to claim 1, wherein said filament element comprises a copolymer.

15. The cerebrospinal fluid ("CSF") collection tube according to claim 1, wherein said filament element further comprises a coating.

16. A CSF collection tube according to claim 15, wherein said coating increases wetability of said filament element.

17. The cerebrospinal fluid ("CSF") collection tube according to claim 15, wherein said coating improves lubricity of said filament element towards CSF.

18. The cerebrospinal fluid ("CSF") collection tube according to claim 15, wherein said coating increases inertness of said filament element towards CSF.

19. The cerebrospinal fluid ("CSF") collection tube according to claim 1, wherein said bottom end portion, said tubular sidewall portion, and said filament element comprise the same polymer or copolymer.

20. The cerebrospinal fluid ("CSF") collection tube according to claim 19, wherein said filament element further comprises a coating.

21. The cerebrospinal fluid ("CSP") collection tube according to claim 20, wherein said coating increases at least one of said filament element's wetability, said filament element's lubricity towards CSF, and said filament element's inertness toward CSF.

22. The cerebrospinal fluid ("CSF") collection tube according to claim 1, wherein said bottom end portion and said tubular sidewall portion are integrally formed.

23. The cerebrospinal fluid ("CSF") collection tube according to claim 1, wherein said bottom end portion is hemispherical.

24. The cerebrospinal fluid ("CSF") collection tube according to claim 1, wherein said bottom end portion is conical.

25. The cerebrospinal fluid ("CSF") collection tube according to claim 1, wherein said tubular sidewall portion is marked with one or more volume graduations.

26. The cerebrospinal fluid ("CSF") collection tube according to claim 1, wherein said bottom end portion, said tubular sidewall portion and said filament element are sterilized.

* * * * *